(12) United States Patent
Weber et al.

(10) Patent No.: US 6,562,054 B1
(45) Date of Patent: May 13, 2003

(54) LIPOSUCTION CANNULAS WITH REMOVABLE MEMORY WIRE

(76) Inventors: Paul J. Weber, 1 Seneca Rd., Ft. Lauderdale, FL (US) 33308; Luiz B. DaSilva, 1995 Camino Ramon Pl., Danville, CA (US) 94526; Michael R. Weber, 13906 Tern La., Clearwater, FL (US) 33762

(*) Notice: Subject to any disclaimer, the term of this patent is extended or adjusted under 35 U.S.C. 154(b) by 223 days.

(21) Appl. No.: 09/625,923

(22) Filed: Jul. 26, 2000

Related U.S. Application Data

(63) Continuation-in-part of application No. 09/203,413, filed on Dec. 2, 1998, now Pat. No. 6,120,519.

(51) Int. Cl.[7] .............................................. A61B 17/30
(52) U.S. Cl. ....................................................... 606/170
(58) Field of Search .......................... 606/35, 127, 170; 600/585

(56) References Cited

U.S. PATENT DOCUMENTS

| | | | | |
|---|---|---|---|---|
| 5,064,428 A | * | 11/1991 | Cope et al. | 606/127 |
| 5,067,489 A | * | 11/1991 | Lind | 600/585 |
| 5,341,818 A | * | 8/1994 | Abrams et al. | 600/585 |
| 5,449,369 A | * | 9/1995 | Imran | 600/585 |
| 5,490,859 A | * | 2/1996 | Mische et al. | 606/159 |
| 5,954,710 A | * | 9/1999 | Paolini et al. | 606/15 |
| 5,980,471 A | * | 11/1999 | Jafari | 600/434 |

* cited by examiner

*Primary Examiner*—Michael J. Milano
*Assistant Examiner*—Gwen Phanijphand
(74) *Attorney, Agent, or Firm*—L. E. Carnahan; John P. Wooldridge

(57) ABSTRACT

Highly flexible liposuction cannulas are constructed of metal and plastic, with the metal cannulas having diameters of between 2.0 and 3.5 mm, and with the plastic cannulas having diameters greater than 3.5 mm (i.e., 3.5 to 9.0 mm). These long shaft flexible cannulas, when utilized in combination with a reinforced neck, allow the cannula point of entry to act as a fulcrum (with an optional interposed insert) and in concert with the surgeon's guiding hand to deflect the cannulas. The cannula tip is preferably highly beveled with an adjacent set of three openings, and the cannula easily penetrates fibrous fat and may reach fast deposits relatively distant from the entrance wounds. The long shaft, highly flexible, reinforced swan neck cannulas move in an easily controllable manner within the subcutaneous tissue below the dermal envelope in an arciform fashion. Benefits include a reduced need to move a patient's body position intraoperatively. The swan neck has been reinforced to provide the needed additional stability at handle/shaft junction to help the surgeon increase leverage on the cannula shaft. The long, flexible plastic cannula shafts are provided central removable metal "memory" reinforcing wires of varying thicknesses along the length thereof which allow controlled rigidity of the long plastic shafts, and enable the cannulas to be bent into a semi-circle without breaking and yet return to their original shape. Removing of the memory wire during autoclaving eliminates thermal damage at plastic/metal interfaces.

22 Claims, 4 Drawing Sheets

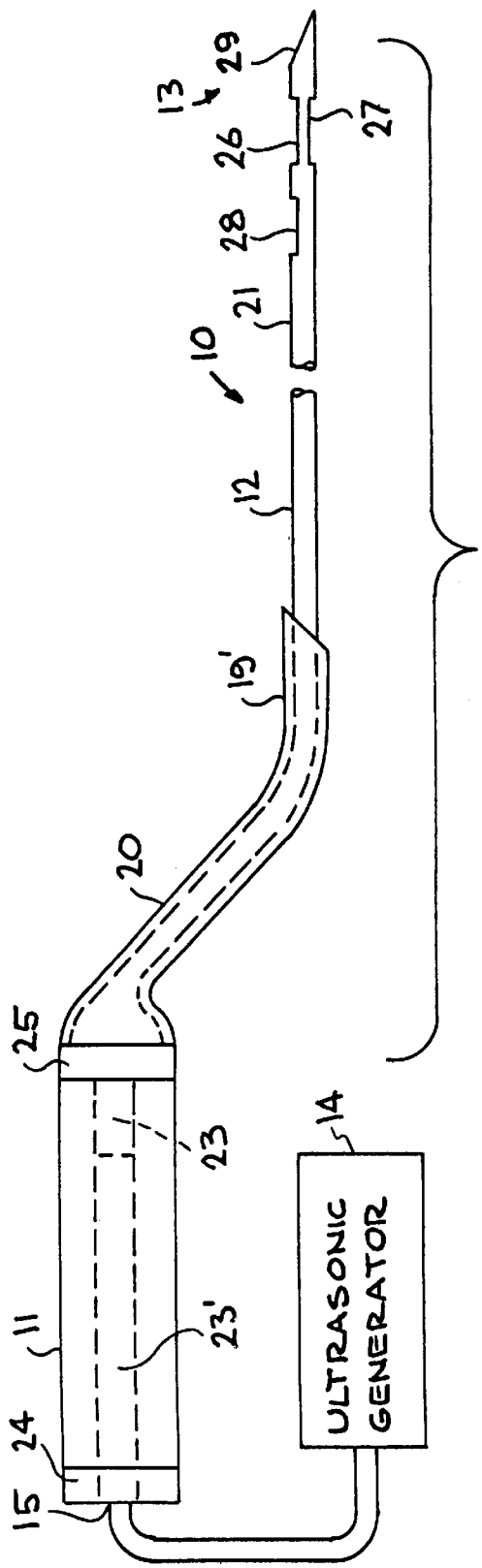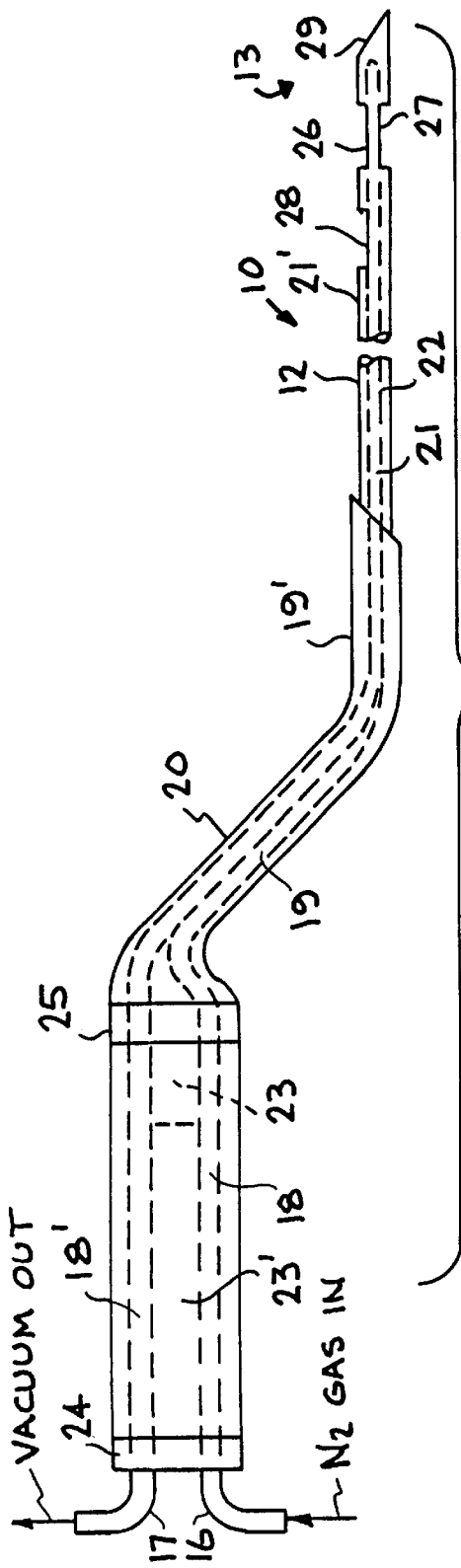

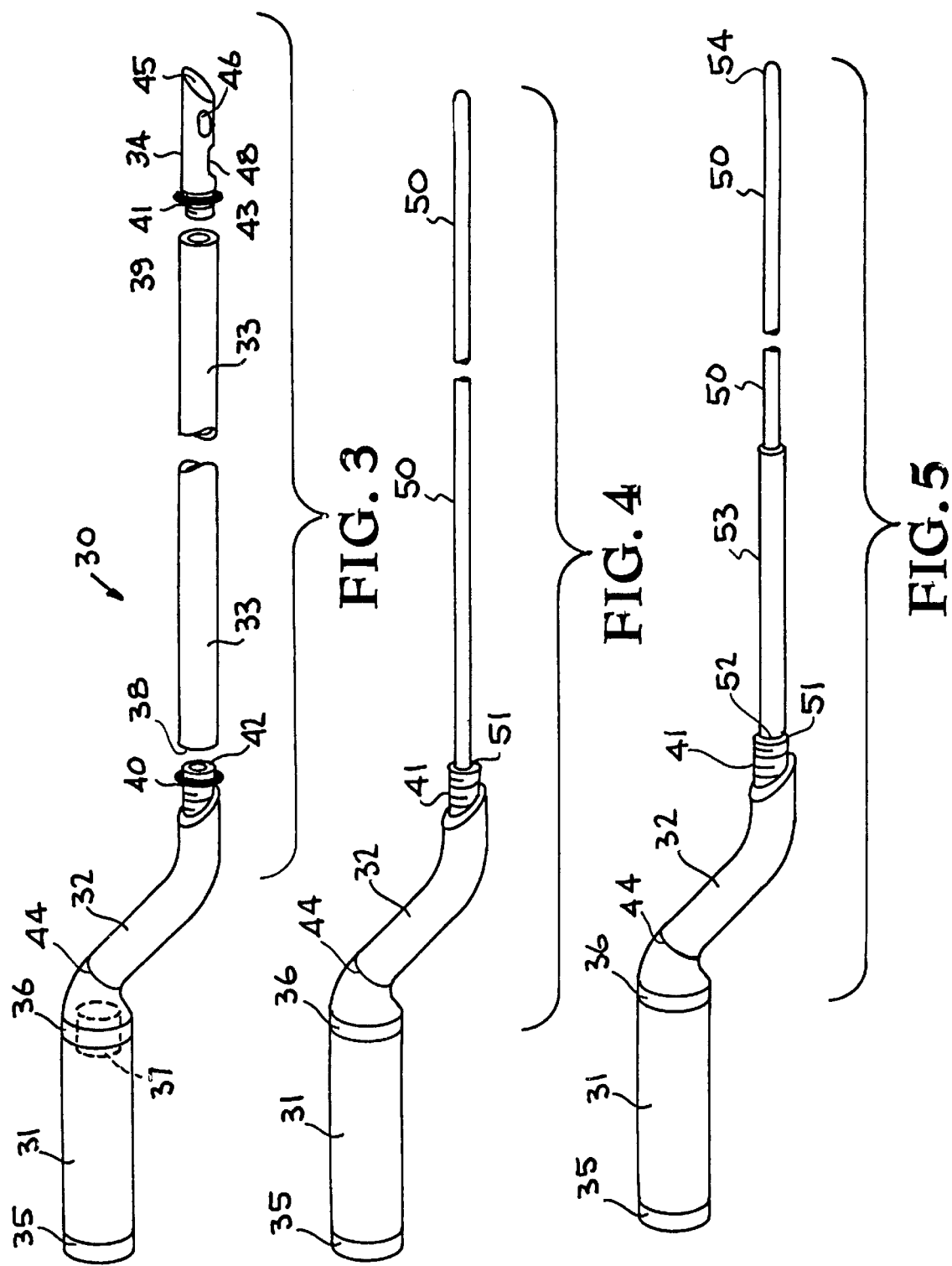

LIPOSUCTION CANNULAS WITH REMOVABLE MEMORY WIRE

RELATED APPLICATION

This application is a continuation-in-part of application Ser. No. 09/203,413 filed Dec. 2, 1998 now U.S. Pat. No. 6,120,519.

BACKGROUND OF THE INVENTION

1. Field of the Invention

This invention relates to a liposuction apparatus and method. Particularly, this invention relates to a liposuction apparatus with the cannula shaft mounted via a swan neck to a handpiece and axial lumen passage, and is ideally suited for smooth continuous fat removal. More particularly relating to long, highly flexible metal or plastic cannula shafts which include a removable metal member.

2. Description of the Prior Art

Liposuction, which literally means "fat suction", is a technique that pulls fat out of the body by means of teasing, pulling, scarping, or suction. It can be used to reduce the volume of fat in many regions of the body, but is particularly effective in areas such as thighs and abdomen, which contain genetically determined fat not responsive to diet or exercise. Liposuction is currently an established modality in cosmetic surgery, performed by surgeons as an elective operation, and is one of the most common procedures in medicine.

All existing ultrasonic liposuction devices used in surgery, especially those with short rigid shafts, can cause complications and trauma by failing to have proper temperature control and improper placement in addition to increased entrance wounding.

A commonly accepted liposuction technique utilizes a cannula with a blunt closed bullet-shaped tip rather than an open tip or a pointed or sharpened tip. This cannula is a metal tube, about the size of a pencil, which is attached to a suction pump. The cannula, with its rounded tip, is sometimes passed though the fat first, without suction, to develop the proper passageway. Then suction is applied and the surgeon continues passing the cannula through the fat tunnels with repeated radial thrusts on several levels of the tissue. Adipose tissue is aspirated through a hole in the side of the cannula near its distal end. The cannula must be moved back and forth through each tunnel. Problems associated with this technique are similar to those experienced with the older methods of liposuction and include: oversuctioning, need for many entrance incisions, difficulty positioning patient, bleeding, and the resistance to passage in fibrous tissues.

Today there exists a wide variety of cannulas which allow surgeons to work more skillfully. For example, there is a bullet shaped tip, or curette-cannula where the suction holes have sharp edges. Rounded or bulbous shaped cannulas, such as bullet or basket-shaped tips, provide three dimensional forces on tissue at the tip which is concentric and conical. The disadvantage of these forces in penetrating highly fibrous fat tissue is that there is likelihood of increasing trauma to these areas vectoring particularly in highly fibrous fat tissue. This force vectoring has the consequence of increasing trauma to these areas. U.S. Pat. Nos. 4,886,491 and 5,514,086 to Parisi et al, both of which are incorporated by reference, describe cannula tips.

A spatula cannula provides a two-dimensional force which allows for greater ease of movement with less exertion on the surgeon's part. The spatula concept has been incorporated into the design of the CAPISTRANO™ line of cannulas. The CAPISTRANO™ cannulas, marketed by Jeffrey Allan Klein, Md., Inc., San Juan Capistrano, Calif., are more rounded and the bevel is oriented more along the center-line and in longer cannulas. Any increase in roundness or bluntness causes increased resistance to passage and thus affords less predictability and bending of an extending probe with patients.

It is also known to use ultrasonically vibrating and aspirating probes in the field of liposuction surgery, as described in U.S. Pat. No. 4,886,491 to the present inventors. The procedure is to introduce the vibrating probe into the area of material desired to be removed which has been preirrigated, and use the ultrasonic vibrations to physically breakup the fatty tissue or loosen it from a fibrous encasement. The fatty tissue can be emulsified by ultrasound and aspirated through the probe, using irrigation as an adjunct. It is known that a particularly effective probe for ultrasonic liposuction is a hollow cylindrical probe with a bullet shaped tip on the distal end. The tip can be welded or otherwise affixed to the probe. Both probe and tip can be manufactured from a variety of acoustically conductive metals such as cold-rolled steel, titanium, and aluminum. In presently known devices, the probe and tip are manufactured from the same materials, or from very similar materials, to ensure effective propagation of the ultrasonic waves all the way to the tip of the probe. Propagation of the waves to the distal tip of the probe is desirable, because this causes the tip of the probe to be able to loosen and emulsify fat, facilitating insertion of the probe into the fatty tissue.

In previously known liposuction techniques, before the use of ultrasound, considerable physical exertion was necessary to force the tip of the probe into the fatty tissue. This was time consuming and required more openings, and it required considerable strength on the part of the physician. The currently known ultrasonic liposuction probes are much more easily moved through the fatty tissue, because the vibrating tip of the probe can loosen the tissue in advance of the probe's shaft passage. This essentially breaks a hole through the fatty tissue, rather than punching a hole by stretching forces.

There is a disadvantage sometimes associated with an ultrasonic probe having an acoustically conductive tip, however. For instance, when the probe has been inserted into the fatty tissue near the skin or the peritoneum, resistance can be met. When resistance is met, the wattage or temperature at the tip increases, and it can increase to the point of damaging the skin or the peritoneum or nerves. During such manipulations, the heat generated at the tip of the probe may be in excess of the ability of the tissues to safely dissipate the heat. In other words, if care is not exercised, the tip may be hot enough to burn tissues, damage muscles, blood vessels, or nerves, and even penetrate membranes such as the skin or peritoneum.

Another problem regarding the liposuction procedure involves the reduction or elimination of friction caused by the motion of the cannula by the surgeon. Applying lubricating jellies and the use of plastic stents are not satisfactory since the jellies must be constantly re-supplied and the plastic stents are difficult to maintain in position. A further problem in liposuction is that most liposuction cannulas are comprised of rigid shafts that are manufactured to be straight without deviation. The human body however is comprised of an outer thin epidermis that overlies the dermis (leather layer of the skin that varies from ⅛ inch to ¼ inch in thickness in most body areas where liposuction is performed). The dermis overlies a layer of suction-able subcutaneous fat that is usually a strip varying from fractions of inches to several inches in thickness depending upon the patient. All three layers epidermis, dermis and fat have one thing in common, that they are curved. Again, unfortunately, liposuction cannulas are straight and rigid with a resulting forceful passage within the patient that does not conform to the curved contour of the target fatty layer or the layer of dermis that contains, envelops, binds or holds the fat in place. The passage of straight, rigid, unbendable cannulas often results in trauma called end hits and is frequently seen during surgery as temporary tents. The net or web of intersecting straight rigid liposuction cannula passages is thus not uniform in density through a curved target of fat.

There remains a need in the art for new devices and methods for removing fatty tissue without damaging skin, nerves, or organs or forming ridges and other disadvantages resulting from conventional or ultrasonic liposuction surgery. A need exists for devices and methods which would greatly assist those practicing liposuction to more efficiently removed unwanted fatty tissue, especially with reduced cannula entrance wounds.

SUMMARY OF THE INVENTION

Factors affecting a surgeon's selection of liposuction shaft length and character may be numerous. These factors may include the following: ease of tip location detection with shorter cannulas, concerns of increased handle/shaft junction breakage with increased length secondary to length-induced leverage, the secondary need for increased shaft diameter to increase strength (durability) when a longer cannula is desired, the advantage of minimizing the number of holes by using longer cannula. The reinforced swan neck allows for an increase range of workable cannula length for a variety of flexible or inflexible metal shaft diameters. These attributes, together with the special tip bevel, allow controllable tissue penetration with novel motions that should reduce the number of entrance incisions, hasten the procedure, reduce the need for patient repositioning. These benefits have been attained without apparent increased bleeding or complications. The use of high memory, extended length cannulas allows for movements and attributes heretofore considered problematic. For example, unique approaches to "hard-to-research" areas, as well as decreasing the number of entry point openings, may modify a surgeon's repertoire.

Along with the tip modification and swan neck modification changes, shaft specifications alterations have been made. The longer stainless steel shafts have been successfully used in all of our liposuctions performed numerous times. Stainless steel shafts in this cannula system are 2.0, 2.5, 3.0, and 3.5 mm in diameter. Currently available stainless steel tubing does not provide the flexibility or memory needed for proper function for shaft diameters exceeding 3.5 mm. However, certain alloys may enable an increase in diameter to about 5 mm.

Although shaft diameters between 2.0 and 3.5 mm provide surprising efficient and aggressive liposuction, many surgeons require cannula shaft diameters exceeding 4 mm to address obese patients and larger liposuction cases. However, metal cannulas with long shafts exceeding 3.5 mm in diameter of stainless steel were found on extensive testing to not possess the desirable qualities of a wide range of flexibility in combination with proper memory. The range for metal shafts is up to about 5.0 mm, preferably about 3.5 mm.

The present invention provides an improved system using plastic cannula shafts with removable internal memory metal support wires which satisfies the need for cannula shafts having diameters of 3.5 mm and up to 8 or 9 mm diameters. The first known use of memory wires in a plastic cannula is described and claimed in applicants U.S. Pat. No. 6,090,121 issued Jul. 18, 2000, entitled "Highly Flexible, reinforced Swan Neck Liposuction Cannulas". This plastic/support wire system has been tested successfully. The invention, as in the above referenced patents allows controlled rigidity of the plastic shafts and the cannulas can be bent into a semi-circle without breaking and yet still return to the original shape due to the internal metal support wire which provides the memory for the plastic shafts. The metal support wire may either decrease in thickness toward the distal end or be mounted via a spheroid-shaped located at the distal end, and may be covered with a Teflon coating to prevent excess load heating during autoclave sterilization of the plastic shaft. The contact of metal and plastic in heat sterilization may cause melting or weakening of the plastic. Removability of the memory wire during autoclave sterilization eliminates any possible reaction between metal and plastic. Also, the reinforced swan neck may be provided with a disconnect which enables ready change of shafts of different diameters. Thus, the plastic cannula shaft system of the present invention, along with the above referenced metal cannula shaft system, provides a surgeon with the tools necessary to perform the complete spectrum of various liposuction procedures.

Straight and rigid liposuction cannula usage results forceful passage within the patient that does not conform to the curved contour of the target fatty layer or the layer of dermis that contains, envelops, binds or holds the fat in place. The net or web of intersecting straight rigid liposuction cannula passages is thus not uniform in density through a curved target of fat. The use of a highly flexible liposuction cannula shaft allows the shaft to curve within the target fatty tissues and within the curviform enveloping dermis. This allows for a more uniform suction effect within the fat and less probing and tangential scraping trauma to the dermis.

SUMMARY OF THE INVENTION

It is an object of the present invention to provide a long highly flexible cannula shaft having a diameter range of about 2 mm to about 9 mm.

A further object of the invention is to provide a liposuction device which includes a reinforced swan neck and a plastic cannula shaft.

Another object of the invention is to provide a liposuction system with a plastic cannula shaft having an internal metal support wire.

Another object of the invention is to provide a plastic cannula shaft with a reinforcing memory wire whereby the shaft can be bent into a semi-circle and returned to its original shape.

Another object of the invention is to provide a swan neck with a coupling arrangement whereby a variety of diameter cannula shafts can be easily connected using a glued seal or O-ring/threads.

Another object of the invention is to provide a plastic cannula shaft with an internal memory wire variable rigidity and thickness. Less flexibility is usually desired at the proximal end than at the distal end of the shaft. Alternatively, uniform flexibility may exist along the shaft length.

Another object of the invention is to provide a plastic cannula shaft with an internal memory wire which is attached at the distal end and is free floating within the plastic shaft.

Another object of the invention is to provide an internal memory wire of a plastic cannula shaft with a thermal protective coating.

Another object of the invention is to provide an internal memory wire comprising a removable spheroid-shaped member(or geometrically shaped distal mass) and wire.

Another object of the invetion is to provide a removable memory wire which can be removed from a plastic cannula during sterilization.

Another object of the invention is to provide a plastic cannula with a removable member (or geometrically shaped distal mass) and wire retained in the cannula tip by a spheroid-shaped member or block and spring arrangement.

Other objects and advantages of the present invention will become apparent from the following description and accompanying drawings. The invention involves highly flexible, reinforced swan neck liposuctions cannulas, and particularly long, flexible cannula shafts that can be bent and return to their original shape. The invention is particularly directed to plastic cannula shafts that exceed 2.5 mm in diameter and which include a removable memory wire. While metal cannula shafts have sufficient flexibility up to a diameter of about 3.5–5.0 mm, plastic cannula shafts have sufficient flexibility in the 2.5–9.0 mm range to enable being bent in a semi-circle and return to the original shape when the plastic shafts include an internal memory wire. The internal memory wire may be constructed so as to be thicker in diameter at the proximal end of the cannula shaft or mounted via a spheroid-shaped member and retainer means at the distal end. In addition, the memory wire may be coated with a heat resistive material while the plastic cannula shaft is steam autoclaved. Ultrasonic energy may energize a portion of the shaft other than the memory wire. Also, the memory wire may be removably attached at the distal end of the cannula shaft and be free floating adjacent the proximal end of the shaft. By providing a removable memory wire, problems associated with sterilization of a plastic/metal assembly are eliminated.

BRIEF DESCRIPTION OF THE DRAWINGS

The accompanying drawings, which are incorporated into and from a part of the disclosure, illustrate embodiments of the invention and, together with the description, serve to explain the principles of the invention.

FIG. 1 is a side view of an embodiment of a liposuction device including a handle removably connected to a hollow, flexible cannula shaft having a high memory of recovery, integrated with a reinforced swan neck and including a triport tip having a bezel, and with the handle connected to an ultrasonic generator.

FIG. 2 illustrates the device of FIG. 1 constructed to be connected to a pressure equalizer and to a vacuum, with the fluid passageways shown in dashed lines.

FIG. 3 is a longitudinal partially exploded view of an embodiment of a liposuction device utilizing a separate swan neck and a removable shaft tip.

FIG. 4 illustrates an embodiment of a metal memory wire to be used in a hollow cannula shaft of high flexibility and memory.

FIG. 5 illustrates the embodiment of FIG. 4 with the metal shaft having an increased thickness at the proximal end, and may be of a thin solid material or a thick hollow material.

DETAILED DESCRIPTION OF THE INVENTION

Figure 7:
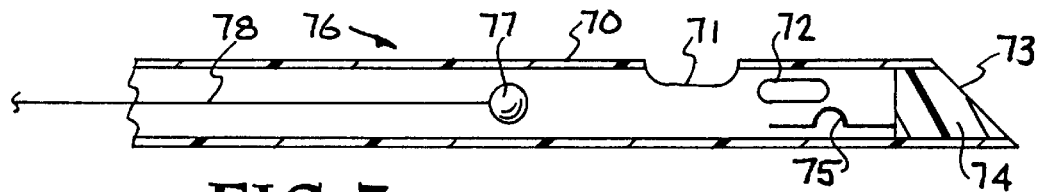
FIG. 7 illustrates a wire/spheroid-shaped member memory wire and an end plug and spring arrangement of a cannula shaft for removably securing the spheroid-shape of the memory wire.

The present invention is directed to highly flexible, reinforced, swan neck liposuction cannulas that, depending on the diameter of the cannula shaft, can be constructed of plastic with a metal memory wire located withing the plastic shaft. Long metal cannula shafts having a diameter of up to about 3.5 mm have some flexibility and can be effectively utilized for various liposuction procedures, but metal cannula shafts above a diameter about 3.5 mm have insufficient non-breaking flexibility and thus only plastic cannula shafts made in accordance with the present invention having an internal memory wire and having diameters of up to about 9 mm can be effectively utilized.

This plastic/memory wire system allows controlled rigidity of the plastic shafts; the cannulas can be bent into a semi-circle without breaking and yet still return to the original shape. Importantly, the plastic shafts must withstand repeated autoclaving or thermal sterilization without being deformed or losing their desirable properties. By removing the memory wire from the plastic shaft before autoclaving each piece separately, any reaction from plastic/metal is eliminated.

Additionally, the liposuction cannula shafts need to be internally reinforced as extensive testing in vivo without reinforcement demonstrated a need for a graded strength along the shaft in more fibrous liposuction patients and locations. The reinforcing "memory" wires may be made to be slightly less flexible in the proximal portions of the shaft and more flexible toward the distal tip, thus allowing a convenient gradation of shaft flexibility. The memory wire may be attached to a spheroid-shaped member (or other geometric shape) that may be removably secured at the distal end. A reinforced swan neck disconnect system is used with any number of different plastic shaft diameters, significantly lowering the cost per unit. The wide range of modified plastic shaft performance makes it possible to predictably suction the mid-lower back from an incision in the umbilicus without rotation the patient on the surgical table while unconscious under sedation or anesthesia, as was previously necessary.

Predictable flexibility and excellent memory are imperatives for the metal and plastic shafts. In this system, it is not preferred that the surgeon should be able to bend a cannula prior to placement into the patient and have the cannula maintain the bent shape. Surgeons that desire this quality may find it available in preexisting systems (bendable malleable cannulas that stay bent and do not spring back) that eventually weaken and require replacement of the cannulas secondary to stress fractures. Also, routine bending by hand is not smooth, regular or uniform, but bumpy and irregular. Also the curves of the body vary from place to place. A permanent bend in a cannula may match only a portion of the curvature in one body location and will usually not match another body location. This problem of natural non-uniform curvatures in the human body requires the surgeon to re-bend these preexisting cannulas to "match the cannula to the contour".

The benefits of increased flexibility and "memory" can be demonstrated in at least two noteworthy behaviors of the new cannula system. The first, called "opposing motion", occurs if less than one-half of the cannula shaft length has been introduced into the patient, then forcing or pointing the cannula handle to the right will move the cannula tip to the left in the patient and vice versa. Lifting the handle will usually direct the tip downward deeper into the patient's subcutaneous tissue. Second, the cannula tip and distal shaft can be made to ricochet (in conjunction with the aforementioned "opposing motion action" exerted by the cannula handle) within subcutaneous fat of the patient.

Most liposuction texts and authorities continue to advocate the spokewheel technique of cannula passage. The spokewheel technique, in essence, may be considered as a series of 90 degree (or any number of degrees) intersecting lines. Another potential benefit of the cannula system of this invention is that by using the principle of "opposing motion action" a surgeon can approximate desirable criss-cross tunneling via increasingly distant entrance wounds.

An apparent benefit of the use of the long, flexible, reinforced swan neck system is the ability to perform liposuction a relatively great distance from the cannula entrance wounds. In patients with a hereditary predisposition to pigment at entrance wounds, this benefit may be significant. Undesirable pink marks can be reduced in fashion models. Typical cannula entrance wound-suction site pairs include the following: posterior flank suctioned from anterolateral abdominal entrance wounds, knees suctioned from superiormost thigh wounds, inner crural thighs suctioned from medial knee wounds, and ankles suctioned from knee wounds. The use of metal 2.5–3.5 diameter cannula appear most helpful in approaching the excess fibrofatty material in the infragluteal area from a medial knee incision in patients who are not over 25% in excess of ideal body weight. For patients who are in excess of this ideal weight parameter, the plastic shaft with reinforcing wire is of benefit. The relatively vertical criss-crossing effect has allowed for ridge free protuberance reduction with no notable buttock ptosis.

There may be disadvantages to the long flexible cannula system. The use of fewer holes to approach more sites will, by necessity, increase the duration of friction and leverage pressure applied to each entrance wound. Longer cannulas, dry operationg room air and proteinaceous material accumulation on the outside of the cannulas can also increase entrance wound friction. The friction may be further increased if a surgeon attempts to use the entrance wound as a fulcrum or use the "opposing motion action" technique. Although all entrance wounds will naturally scar, those that are traumatized the most will remain pigmented the longest, especially in pigment prone patients.

Aside from coating the external portion of cannula shafts with non-stick polymers (that eventually wear off) and applying lubrication jellies to the entrance wounds, another solution to the entrance wound friction problem is the use of temporary intraoperative plastic stents or anti-friction means. Unfortunately, previously available screw-in devices are of thicker materials and damage skin entrance wounds via pressure more than the anti-friction means hereinafter.

The preferred anti-friction means is a conical Teflon. The insert is of low friction inside (to aid in cannula passage) and higher friction outside (to reduce the tendency to extrude on cannula backstroke) and can be easily and quickly applied to or removed from any size liposuction entrance wound. Outside friction is increased predictably as a result of projections, unidirectional notches or slits in the insertional exterior portion of the anti-friction means. The non-insertional portion of the anti-friction means may have a single row of oppositely directed notches or slits to prevent over insertion of the device.

Figure 2A:
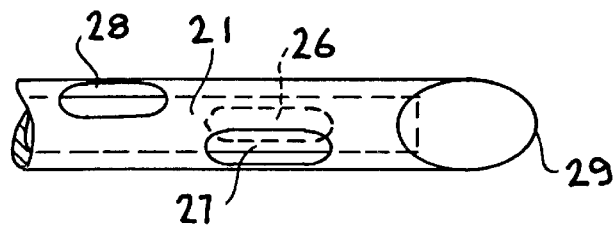
FIG. 2A is a partial top view of an embodiment of the multi-port tip of FIGS. 1 and 2.
Figure 2B:
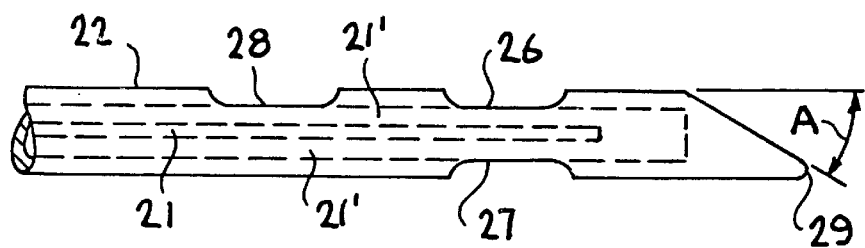
FIG. 2B is a partial side view of the multi-port tip of FIG. 2A illustrating the fluid passageways in dashed lines.

Referring now to the drawings, FIGS. 1, 2, 2A and 2B illustrate an embodiment of a liposuction device (generally indicated at 10) which includes a handle or handpiece (generally indicated at 11) and an integral reinforced swan neck/cannula shaft (generally indicated at 12) with the cannula shaft having a tip section(generally indicated at 13). As shown in FIGS. 1 and 2, the handpiece 11 is connected to an ultrasonic generator 14 via a coupling 15, to a fluid supply (such as N2 gas) via a connection tube 16, and a vacuum source via a connection tube 17. As shown in dashed lines in FIGS. 2 and 2B, the handpiece 11 includes a channel or tube 18 connected to a channel or tube 19 in reinforced swan neck section 20 and channel or tube 21 in cannula shaft section 22 of the reinforced swan neck/cannula shaft for direction fluid material through the handpiece to the tip section 13, which is suctioned out via a channel or tube 19' and a channel or tube 18'. The fluid cooling, aspiration and ultrasonic arrangements for the device 10 are known in the art and further detail is deemed unnecessary. The handpiece 11 also contains a microprocessor 23 located in a channel 23' (shown by dash lines) for controlling fluid passage through the device 10.

The handpiece 11 also includes removable (threaded) end sections 24 and 25 which are connected to the coupling 15 and connection tubes 16 and 17 and to the reinforced swan neck section 20, the shaft section 22 being fixedly secured in or integrally formed with the reinforced swan neck section 20. The fluid connection 16 is connected to a tube 18 (indicated by dash lines) which extend via a connection to tube 19 in the reinforced swan neck section 20 to the tip section 13 (as seen in FIG. 2B) whereby cooling or cleaning fluids may be introduced at the tip section 13. If desired, the handpiece 11 and swan neck section 20 may be connected by commercially available quick connect assemblies.

Tip section 13 of cannula shaft 22 is of a triport type with a beveled end or bezel. As seen more clearly in FIGS. 2A and 2B, the tip section includes a pair of openings 26 and 27 and a third opening 28 spaced from openings 26 and 27, and a tapered or beveled end or bezel 29 having an angle (A) of inclination of about 20 to 60 degrees, preferably about 35 degrees.

The swan neck section 20 is reinforced for several reasons. Reinforcement provides the needed stability to help a surgeon increase leverage on the cannula shaft section 22 and to use it as a guide in combination with the wound opening. The reinforcement may consist of a flexible thickening material (such as thermoplastic or thermoset polymers) or a wire reinforcement or a metallic sleeve or jacket cannula. Preferably, the reinforcement comprises a thickening. The shaft is constructed of a material having excellent flexibility and memory characteristics. Metals and plastics are suitable materials of construction. Examples of plastic material include olefin polymers, fluorocarbon polymers and synthetic rubbers. Preferably polypropylene, polyethylene and tetrafluoroethylene, and more preferably high-density polyethylene, are utilized. Examples of suitable metals include aluminum, cold rolled steel, stainless steel, titanium, or a titanium alloy.

As pointed out above, the cannula shaft section 22 is constructed of metal (such as stainless steel or non oxidizing alloys) with a diameter of about 2.0–3.5 mm and up to about 5.0 mm. The shaft section 22 is sufficiently rigid to permit repeated and controlled advancing strokes through the tissue but is sufficiently flexible to enable an amount of bending. The reinforced swan neck section 20 allows for longer insertional lengths of the shaft section 22 (which range from about 15 cm to about 35 cm, and preferably from 25–33 cm). The excised tissue from the surgical site is aspirated via channels 21', 19' and 18' to a vacuum line 17 and to a collection means (not shown). Irrigating fluid (such as saline, antiseptic, anesthetic solutions, hyaluronidase, heparin, and epinephrine) or cooling fluid such as an inert gas (nitrogen, for example) are directed through tube 16 and channels 18, 19, and 21 to tip section 13, and are aspirated out with the removed fatty tissue.

FIG. 3 illustrates an embodiment of a liposuction device wherein the cannula shaft is removably connected to the swan neck, the swan neck is removably connected to the handpiece, and the tip is removably connected to the cannula shaft. As shown, the device (generally indicated at 30) basically includes a handpiece 31, a swan neck 32, a cannula shaft 33 and a triport beveled tip 34. Handpiece 31 includes removable end 35 and 36, with a microprocessor 37 mounted in end 36. Shaft 33 is provided at each end 38 and 39 with internal threads that cooperate with threaded end 40 of swan neck 32 and threaded end 41 of tip 34. A pair of O-ring seals 42 and 43 are located about threaded ends 40 and 41. While not shown, swan neck 32 is threadedly connected at 44 to a removable end 36 of handpiece 31 in a similar manner. Tip 34 includes a beveled end 45 and three openings (as in FIGS. 2A–2B) with only two openings shown (46 and 48). The cannula shaft 33 and tip 34 is preferably made of metal if the diameter is less than about 3.5 mm, or made of plastic if the diameter is greater than about 3.5 mm.

If the cannula shaft of FIG. 3 is constructed of plastic with a diameter greater than about 3.5 mm, a flexible metal guide shaft or memory wire (as shown in FIG. 4) is located internally to provide memory for the plastic shaft (to return it to its original shape after bending). Components of FIG. 4 corresponding to FIG. 3 are given corresponding reference numerals. As seen in FIG. 4, a memory wire or guide shaft 50 is secured in an opening 51 of the threaded end 40 of swan neck 32, with wire 50 being of a smaller diameter than the inner diameter opening 51 of end 40 to allow passage of fluids and/or aspiration of fatty tissue to pass therebetween, or the memory wire 50 may be made hollow to provide an aspiration path.

To enable the plastic cannula shaft to bend up to a semi-circle and return to its original position, it is preferred that the memory wire or guide shaft of FIG. 4 have a thicker proximal end than distal end. FIG. 5 illustrates an embodiment wherein the proximal end 52 of the wire 50 of FIG. 4 is provided with a metallic coating 53. If desired, the wire 50 may be tapered or contain tapered sections with decrease from the proximal end 52 to the distal end 54.

Figure 6:
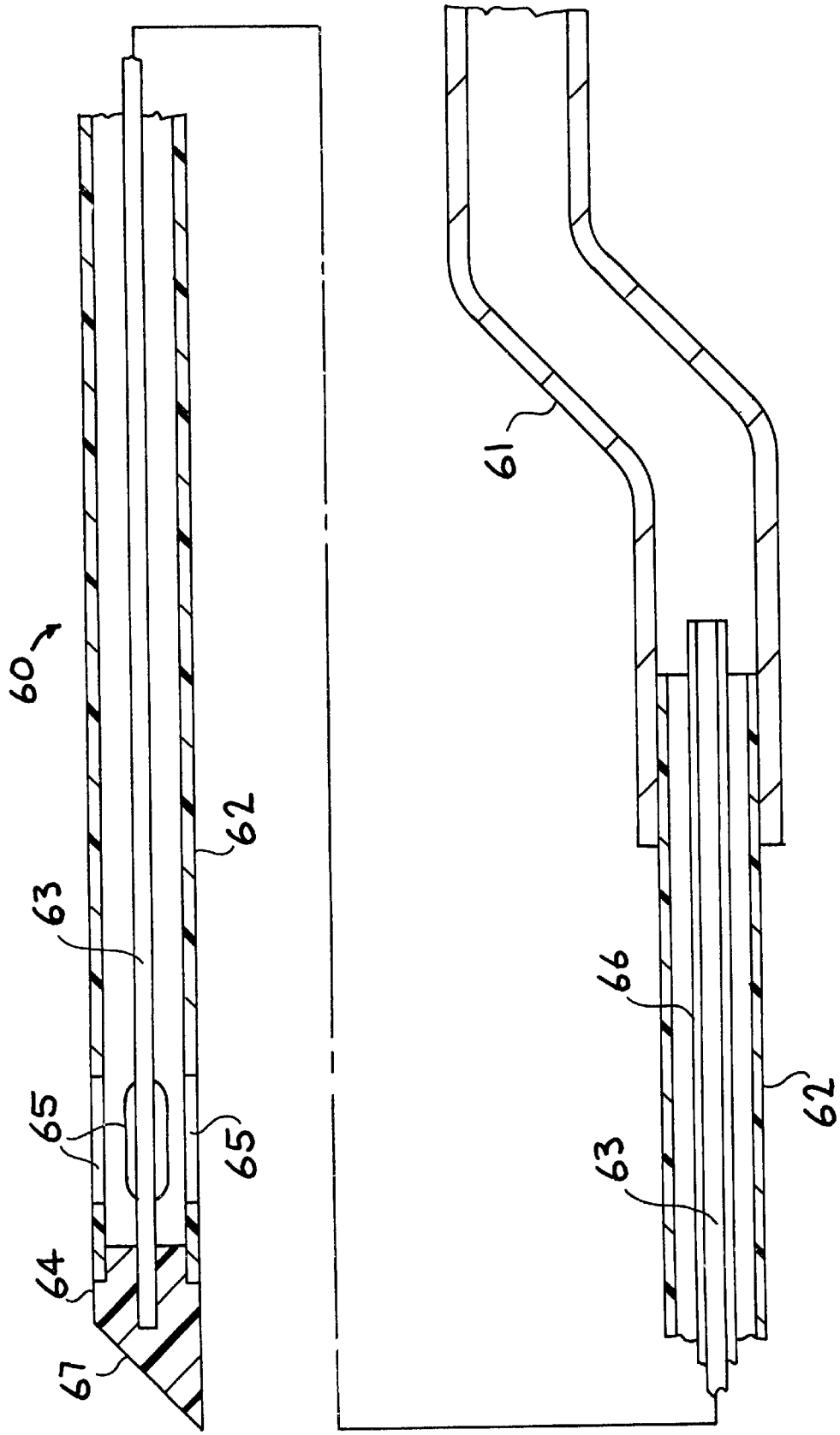
FIG. 6 illustrates an embodiment of a plastic cannula shaft which may be removably secured in the swan neck and including a free floating memory wire secured to the shaft at the distal end.

FIG. 6 illustrates an embodiment of a free-floating memory wire for a plastic cannula tube having a diameter of greater than about 3.5 mm.

As shown in FIG. 6, a swan neck/cannula shaft generally indicated at 60 comprises a swan neck 61 and a plastic cannula shaft 62 that is secured to or integral with swan neck 61. A free floating metal memory wire 63 is mounted within cannula shaft 62 via a plug 64 located near the distal end of shaft 62, which is provided with one or a plurality of openings 65, and plug 64 includes a beveled end 67 (as in FIGS. 2A–2B). The memory wire 63 is provided with an increased thickness or layer 66 at the proximal end of shaft 62. The memory wire 63 extends into the swan neck 61 but terminates short of the first bend therein (as shown). By way of example, the plastic cannula shaft 62 has a diameter of from about 3.5 mm to about 9.0 mm, with the memory wire 63 being constructed of stainless steel with a diameter of ½ mm to 6 mm and the layer 66 may be composed of stainless steel with a diameter of 1.5 mm to 6.5 mm, with plug 64 composed of PEEK (polyarylether ketone polymer) made by Victrex, Westchester, Pa., plastic Delrin, epoxy or glue. The memory wire 63 and layer 66 may be integrally fabricated, if desired. Shaft 62 may terminate in a beveled or bezel tip 67 which may be constructed as shown in FIGS. 1–2B or FIG. 3.

Figure 8:
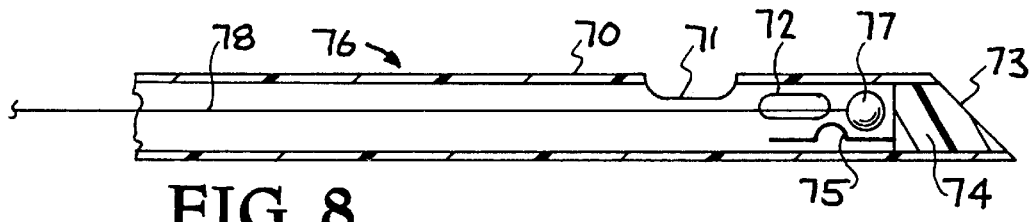
FIG. 8 illustrates the spheroid-shape of the wire/spheroid-shaped member memory wire of FIG. 7 mounted in the spring and end plug of the cannula shaft.
Figure 9:
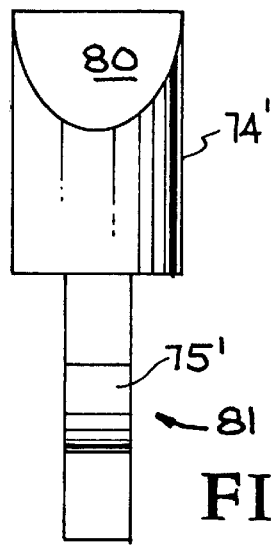
FIGS. 9 and 10 illustrate top and bottom views of the plug/spring arrangement of FIGS. 7 and 8.
Figure 10:
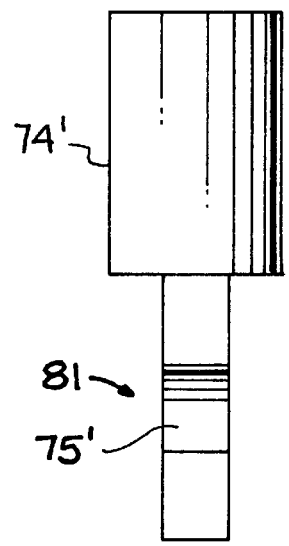

FIGS. 7 and 8 illustrate an embodiment of the present invention wherein a memory wire composed of a spheroid-shaped member and wire are removably mounted in the distal end of a cannula shaft via a plug and spring arrangement, with FIGS. 9 and 10 illustrating top and bottom views of the end plug/spring.

As seen in FIGS. 7 and 8, a cannula shaft 70 is provided, as in FIG. 6, with distal end openings 71 and 72 and a beveled or tapered end 73. Mounted within the beveled or tapered end 73 is a plug 74 having a member 75 secured thereto which functions as a spring to removably retain a memory wire 76 composed of a spheroid-shaped member 77 and a wire 78. The plug 74 may be constructed of plastic or resin and is secured as by gluing, or ultrasonically sealing in the end 73 of cannula shaft 70. As shown in FIG. 7, the memory wire 76 is removed from spring member 75 to enable separate cleaning or sterilization of the cannula 70 and the memory wire 76. As shown in FIG. 8, the spheroid-shaped member 77 of memory wire 76 is retained by the spring member 75. The memory wire 76 may be of a free-floating type as in FIG. 6 or may extend into the swan neck with the diameter thereof being smaller adjacent the spheroid-shaped member 77.

FIGS. 9 and 10 illustrate top and bottom views of a plug 74' having a spring member 75' for retaining the spheroid-shaped member 77 of the memory wire 76 and FIGS. 7 and 8. As shown the plug 74' includes a beveled or tapered surface 80 which corresponds to the configuration of an end 73 of cannula shaft 70, for example. The spring member 75' may be made integral with plug 74' or secured thereto, and includes a hump 81 therein over which the spheroid-shaped member 77 of memory wire 76 passes and is removably retained between the hump 81 and the plug 74' when mounted in a cannula shaft. Thus, the spring member 75 or 75' enables easy removal of the memory wire 7 from the cannula shaft 70 for sterilization.

While not shown, the spring member may be constructed in the form of a hollow tube composed of flexible/expandable material with the spheroid-shaped member of the memory wire inserted into the end of the flexible tube. It has thus been shown that the present invention provides a liposuction device that can be effectively utilized with various diameter cannula shafts, and wherein plastic cannula shafts with removable memory or guide wires are effectively utilized wherein shaft diameter or greater than about 2.5 mm are desired. By providing removability of the memory wires, problems associated with metal/plastic reactions during sterilization are eliminated. The spheroid-shaped member/wire and retainer member provide a simple, inexpensive approach for removably retaining the memory wire.

While a particular embodiment has been illustrated and described, such is not intended to be limiting. Modifications and changes may become apparent to those skilled in the art, and it is intended that the invention be limited only by the scope of the appended claims.

What is claimed is:

1. In a liposuction device having a handpiece, a reinforced swan neck, and a flexible cannula shaft, the improvement comprising:

a removable memory wire operatively mounted in said cannula shaft, said memory wire being constructed and mounted to return the cannula shaft to an original position after being flexed.

2. The improvement of claim 1, wherein a distal end of said removable memory wire is removably secured at a distal end of said cannula shaft.

3. The improvement of claim 2, wherein said cannula shaft includes means secured at said distal end for removably retaining said memory wire.

4. The improvement of claim 3, wherein said means includes a spring member.

5. The improvement of claim 4, wherein said spring member is integral with or secured to a plug mounted in said distal end of said cannula shaft.

6. The improvement of claim 3, wherein said memory wire comprises a spheroid-shaped member and wire, and wherein said spheroid-shaped member is removably retained by said means.

7. The improvement of claim 6, wherein said means is constructed to flex for retaining said spheroid-shaped member.

8. The improvement of claim 7, wherein said means comprises at least one spring member which results in a constriction to allow said spheroid-shaped member to pass over a section thereof.

9. The improvement of claim 8, wherein said spring member is secured to or integral with a plug located in a distal end of said cannula shaft.

10. The improvement of claim 1, wherein said cannula shaft is removably mounted to a swan neck handpiece.

11. The improvement of claim 6, wherein said spheroid-shaped member is chosen from the group of shapes including sphere, polyhedral, conical, geodesic, spheroid, and irregular geometric shapes.

12. A liposuction device including: a handpiece, a reinforced swan neck, a flexible cannula shaft mounted to said reinforced swan neck, and a removable memory wire mounted in said cannula shaft for providing internal reinforcement of said cannula shaft, said memory wire being constructed and mounted to enable return positioning of said cannula shaft when flexed.

13. The device of claim 12, wherein said removable memory wire comprises a spheroid-shaped member and wire, said spheroid-shaped member being removably retained adjacent a distal end of said cannula shaft.

14. The device of claim 13, wherein said spheroid-shaped member is removably retained by a spring member.

15. The device of claim 14, wherein said spring member is mounted to a plug located in said distal end of said cannula shaft.

16. The device of claim 13, wherein said removable memory wire is removably retained at one end in a distal end of said cannula shaft.

17. The device of claim 16, wherein said removable memory wire includes a spheroid-shaped member at said one end, said spheroid-shaped member being removably retained in said distal end of said cannula shaft.

18. The device of claim 17, wherein said spheroid-shaped member is removably retained by a spring member.

19. The device of claim 18, wherein said spring member is mounted to or integral with a plug secured in said distal end of said cannula shaft.

20. The device of claim 12, wherein said flexible cannula shaft is constructed of plastic.

21. The device of claim 12, wherein said removable memory wire contains areas of different flexibility.

22. The device of claim 12, wherein said removable memory wire includes a gradation of flexibility between proximal and distal portions thereof.

* * * * *